(12) United States Patent
Von Meyer

(10) Patent No.: US 7,550,654 B2
(45) Date of Patent: Jun. 23, 2009

(54) METHOD FOR EXPANDING CORN EAR TIPS TO INCREASE SEED YIELD THROUGH RECESSIVE GENETIC DETERMINANTS

(75) Inventor: William C. Von Meyer, Pendleton, SC (US)

(73) Assignee: Fairview Industries, Inc., Pendleton, SC (US)

( * ) Notice: Subject to any disclaimer, the term of this patent is extended or adjusted under 35 U.S.C. 154(b) by 363 days.

(21) Appl. No.: 11/220,275

(22) Filed: Sep. 6, 2005

(65) Prior Publication Data

US 2006/0053511 A1    Mar. 9, 2006

Related U.S. Application Data

(60) Provisional application No. 60/607,991, filed on Sep. 8, 2004.

(51) Int. Cl.
| | |
|---|---|
| A01H 5/00 | (2006.01) |
| A01H 5/10 | (2006.01) |
| A01H 4/00 | (2006.01) |
| A01H 1/00 | (2006.01) |

(52) U.S. Cl. .................... 800/320.1; 800/260; 800/266; 800/275

(58) Field of Classification Search ................. 800/260, 800/266, 275, 320.1
See application file for complete search history.

(56) References Cited

U.S. PATENT DOCUMENTS

| | | | |
|---|---|---|---|
| 4,351,130 A | | 9/1982 | Rutger et al. |
| 4,513,532 A | | 4/1985 | Muirhead, Jr. et al. |
| 4,731,499 A | * | 3/1988 | Puskaric et al. .......... 800/320.1 |
| 5,476,999 A | | 12/1995 | McConnell et al. |
| 6,018,101 A | | 1/2000 | Zhang et al. |
| 6,368,806 B1 | | 4/2002 | Openshaw et al. |
| 6,642,441 B2 | | 11/2003 | Brokish |
| 6,765,133 B2 | | 7/2004 | Koehring |
| 6,914,177 B1 | | 7/2005 | Colbert et al. |

OTHER PUBLICATIONS

Rentao Song and Joachim Messing, Gene expression of a gene family in maize based on noncollinear haplotypes, Proc. National Acad. Science, Jul. 22, 2003, p. 9055-9060, vol. 100, No. 15, U.S.A.
J.H. Kempton, Heritable Characters in Maize, Journal of Heredity, 1934, vol. 25, p. 29-32, U.S. Department of Agriculture, U.S.A.
E.J. Wellhausen, et al., Races of Maize in Central America, 1957, pub. 511, National Academy of Sciences-National Research Council, Washington, DC, U.S.A.
O.E. Nelson, Jr., et al., Am. J. Botany, 1954, vol. 41(9), p. 739-748, U.S.A.
Roberto Tuberosa, et al., Mapping QTLs Regulating Morpho-physiological Traits and Yield: Case Studies, Shortcomings and Perspectives in Drought-stressed Maize, 2002, p. 941-963, Annals of Botany Company, U.S.A.
G.N. Collins, Hybrids of Zea Ramosa and Zea Tunicata, Journal of Agricultural Research, Jun. 11, 1917, vol. IX, No. 11, p. 383-395, Washington, DC, U.S.A.

* cited by examiner

*Primary Examiner*—Medina Ibrahim
*Assistant Examiner*—Keith O. Robinson
(74) *Attorney, Agent, or Firm*—McNair Law Firm, P.A.; Seann P. Lahey

(57) ABSTRACT

This invention provides a novel means of making maize hybrids and inbreds with expanded ear tip phenotypes for promoting increased seed yield from recessive genetic determinants. This is achieved by making standard inbred×hybrid as well as inbred×inbred crosses followed by selection in the subsequent self-pollinated generations from these plants for expanded ear tip phenotype characteristics to produce new parent inbred lines. Next, the resulting inbreds, having a different pedigree but possessing the recessive expanded ear tip genetic determinants, are crossed to cause the expanded ear tip trait to express as a homozygous recessive trait in an otherwise primarily heterozygous hybrid.

27 Claims, No Drawings

METHOD FOR EXPANDING CORN EAR TIPS TO INCREASE SEED YIELD THROUGH RECESSIVE GENETIC DETERMINANTS

CROSS REFERENCE TO RELATED APPLICATION

This application claims the benefit under 35 U.S.C. 119 of provision application 60/607,991 filed Sep. 8, 2004.

BACKGROUND OF THE INVENTION

1) Field of the Invention

The present invention relates to maize plants having increased seed yield, and more particularly, to a method for producing inbred and hybrid corn plants having the phenotypic property of expanded corn ear tips for providing increased seed yield based on a recessive genetic system for trait selection.

2) Description of Related Art

Corn is the most extensively grown of all grain crops in the United States. It is of great agricultural and economic interest to provide new corn inbreds and hybrids which display an improvement in particular characteristics, such as increased seed yield, disease resistance, standability, tolerance to environmental factors, and the like. Through proper breeding techniques, these characteristics can be introduced into new or existing inbred lines of maize which can then be used to produce superior hybrid corn, which is the predominant commercial type.

Many years ago plant biologists and naturalists noted that when diverse strains of maize were crossed or hybridized, their vigor increased. This response became known as hybrid vigor or heterosis. In focusing on increased seed yield, prior efforts in heterosis and maize genetics led to a treatment of increased seed yield as being due specifically to numerous dominant and additive gene actions for beneficial effects on kernel weight, kernel number per ear, and ears per plant and unit land harvested.

In modern breeding, the complexity of corn genes affecting yield have been largely discussed under the heading of QTL's or "quantitative trait loci." The entire corn growing ecosystem and plant response has since been modeled into various genetic determinants (see J. T. Richie and G. Alagarswamy, Agronomy J. 95:4-9, 2003. Am Soc. Of Agronomy). However, the specific manipulation of determinants or a single determinant in a complexity of gene interactions is very difficult. It would be extremely useful if one could change the hybrid corn plant ear to increase kernel number per ear without altering the remainder of beneficial traits of a hybrid such as heat tolerance, disease resistance, fertilizer efficiency and so forth.

In corn, parent strain selection for higher yield in hybrid crosses has mainly involved large numbers of inbred lines being formed and their subsequent testing as hybrids for heterosis toward higher yield. Plants that have been self-pollinated and selected for type for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of loci will produce a population of hybrid plants that differ genetically and will not be uniform.

The development of superior corn hybrids requires the development of homozygous inbred lines, the crossing of these lines, and the evaluation of the crosses. The goal of corn breeding is to develop new, unique and superior corn inbred lines and hybrids. In pedigree selection breeding, the breeder combines the genetic backgrounds of two or more inbred lines or various broad-based sources into breeding pools from which the new inbred lines are developed by selfing and selection of the desired phenotypes. The new inbreds are crossed with other inbred lines and the hybrids from these crosses are thoroughly tested and compared to appropriate standards in environments representative of the commercial target area(s).

Pedigree selection breeding starts with the crossing of two genotypes, each of which may have one or more desirable traits or more desirable characteristics that are lacking in the other or which complement the other. If the two original parents do not provide all of the desired characteristics, other sources can be included in the breeding population. In the pedigree selection method, superior plants are selfed and selected in successive generations. In the succeeding generations, the heterozygous condition gives way to the homozygous lines as a result of self-pollination and selection.

Hybrid vigor has been the major means to enhance yield for more than 75 years. The general hypothesis behind heterosis is that the genetic loci on the DNA strands of the ten chromosomes of maize cooperate better when they are from different parents of different composition. Inbreeding has been found to specifically reduce seed yield.

In corn, the product of inbreeding is termed an "inbred" or "inbred line" of which there have been hundreds of thousands of bushels sold or employed as parents for hybrids. Inbreeding is typically accomplished by self-pollination as described above. At each self-pollination the number of heterozygous progeny loci is reduced by 50%. Eventually, after several generations of selfing, a progeny row from a single ear will appear very uniform and individuals are almost indistinguishable to the eye. Generally, after 6-10 selfings, a line is typically considered ready for use in hybrid manufacturing because the character of the plant is highly reproducible at that point.

Backcrossing is another means of inbreeding and inbred production. Four to six backcrosses of a random corn plant by an inbred may produce a uniform inbred population with the traits of the recurrent parent, except for those traits selected as different from the recurrent parent in each generation of backcrossing. For recessively inherited traits, after each backcross a cycle of self-pollination is useful. Inbreeding a heterozygous plant or population or backcrossing an inbred to a heterozygous plant or population is known to result in decreased yield. This has been attributed to the uncovering of deleterious recessive genes or breaking up a cooperative beneficial heterozygous loci.

In commercial breeding when two candidate inbred parents are crossed and fail to show hybrid vigor, that combination is discarded as a hybrid candidate. Inbred parent seeds are marketed based on units of 1000 viable kernels or MVK. Thus, for an inbred, a means of increasing seed number per harvested whole ear is an important matter effecting cost of parent seed production. "Seeds per acre" is also an important component of hybrid yield.

There are several thousand genes in the maize genome and these are forming as the genome evolves each year through both natural and artificial means. Some studies relating to the genomics of yield have concluded that most traits of interest to the maize breeder are strongly affected by the environment and necessitate complex and costly experimental designs for their definition. The concern of much of the genome research is with the identification and manipulation of traits which are effected by several genes, the so called QTL's. Interim results have indicated that large numbers of small loci may effect such a parameter as the yield×environment interaction. (see S. J. Oppenshaw and E. Frascaroli, Proceedings of the 52$^{nd}$ Annual Corn and Sorghum Research Conference 44-53. 1997. *QTL detection and marker assisted selection for traits in maize*).

It would thus be desirable to isolate genes in inbred lines which affect a valued component of yield without such multi-locus complexity. At the present time, one cannot simply pick out a gene and then increase it per se in any average maize plant to give a higher seed yield result. Among the problems in doing this is that the existence of a unit of DNA does not ensure its expression in the complex milieu of a plant. Single genes which affect yield by increased disease resistance are known but these are generally regarded as auxiliary traits not directly reading on ear or plant morphology. Multi-gene traits such as vertical leaf habit or strong stalks can be considered a component of yield. A simply inherited genetic determinant has not been identified which in isolated use determines a quantitative result for increased yield in hybrid form until the present invention.

What makes finding determinants to increase yield difficult for a person skilled in the art is: 1) development and isolation of pure breeding strains carrying the trait, requires several years; 2) crossing the inbreds to achieve pollen and silk nick without interference from outside elements; 3) harvesting the viable hybrid seed; 4) planting and succeeding in growing out the progeny in such a manner that phenotypic traits of the hybrid can be measured. The current products of the hybrid maize breeder, as to the shape and form of the hybrid maize seed bearing ear (the female inflorescence or flower), fall into one of the following simple descriptions or categories: 1) largely parallel side ears as a result of the seeds occurring on parallel sided cobs with the butt of the ear nearest the stalk shaped in a blunt manner and slightly larger in diameter than the distal tip of the ear; 2) slightly conical or moderately conical ears with the distal tip of the ear decidedly smaller than the base of the ear, and the tip of the ear having fewer kernels than the base, with the sides of the ear not parallel. Ears of tropical and exotic maize have been reported with various shapes; however, none of the heritable determinants or genes have been employed to make a controlled ear morphology with useful yield effect in a subsequent single cross hybrid, backcross hybrid, or double cross hybrid.

The ramosa allele is an example which modifies maize ears by various split shapes in tropical varieties where it was described. Small split ears or furcated ears were derived from the variety Quicheno Ramoso and their origin was the McBryde Collection #26 and #47. A practicum for the use of the ramose gene in maize in finding a single recessive genetic mechanism for increasing maize yield improvement has yet to be presented. Further, there has not been any suggestion that hybrid or inbred maize ears with useful modified ears could be developed from crosses with standard maize plants. Accordingly, there has not been any described or implemented practical means of using the ramose type effect for enhancing plant yield.

The prior art fails to disclose any prescribed use of the heritable genetic determinants known to effect the morphology of the corn ear tip in the improvement or management of plant seed yield. Thus, the commercial production of maize as a single cross hybrid, three-way cross hybrid, backcross hybrid, double cross hybrid or parent inbred has not been accomplished wherein the tips of the corn ear, or a large percentage of ears, in a field or row of plants employed commercially, are routinely larger than the base or the mid portion of the ear, and wherein the tip of the ear contributes significantly more to yield than a normal shaped ear in the same family.

Heretofore, maize breeders have neglected the intentional manipulation of ear tip phenotypic traits through recessive genetic determinants to provide for expanded ear tips. All currently employed hybrids and open pollinated varieties lack enlarged ear tips in any significant percentage of their population. Such a feat as to be able to routinely make hybrids with a large percentage of the plants having expanded ear tips will provide more harvestable tissue mass per acre planted.

Accordingly, it is the object of the present invention to provide a method for producing a hybrid and inbred corn ears having an expanded ear tip larger that the base of the ear which results from the selection of recessive trait(s) in the breeding process, said traits when combined in the hybrid result in enhanced seed yield.

SUMMARY OF THE INVENTION

The above objective is accomplished according to the present invention by providing a procedure and means of producing hybrid, backcross, and inbred ears with larger tip tissue and greater seed yield per plant than standard conical or parallel sided maize ears using standard pure line inbred parents which lack such expanded ear tip trait.

In general the method involves identifying a means of forming and isolating a recessive trait in an isolated inbred parent which effects in a positive manner ear seed yield. This is accomplished by the introduction of "spo" determinants, which confer expanded ear tip phenotypes, into each parent of the hybrid before crossing. A double benefit is obtained from the higher seed yield of the inbred as well. The breeding method disclosed herein is the opposite of most common breeding procedures for enhancement of yield in maize, i.e. that of combining many dominant diverse genes in a hybrid for yield enhancement resulting in heterosis or hybrid vigor. Rather, the invention focuses on the development of a recessive determinants through selection and combining the recessive trait in the hybrid and inbred to manufacture a corn ear with an expanded tip, and using the expanded ear tip to also enhance the yield.

The present invention employs well adapted pure line inbred parents with normal ear tips in crosses between themselves and a normal eared hybrid, or normal eared heterozygous population, to derive a modified ear tip maize plant as an inbred parent. The resulting parent(s) which have enlarged ear tips, termed "spo" ears may then be employed as hybrid parents or to make further "spo" eared inbreds and hybrids. The entire prior art of maize breeding fails to direct attention to the ear tip as a primary target for enhancement of yield, particularly through recessive genetic determinants.

The method of the present invention is also different from the prior art in that a single or a few closely linked recessive genetic determinants are isolated by phenotypic analysis during selfing of a heterozygous family. A large yield effect is accomplished in the hybrid plant by the single or closely linked recessive determinant when brought together in the hybrid. This may be termed recessive single trait locus enhancement (RSTLE). Most maize breeders in contrast are seeking dominant favorable loci. From the specified use of what is term a "spo" determinant for purposes of the present invention, or heritable genetic determinant for expanded corn ear tip, made by the process of selection described herein, the expanded ear tip would not express unless both parents possessed the recessive "spo" determinant. Thus, the method of enhancing yield by the present invention is contrary to the dominant favorable allele theory except that dominant favorable alleles may favorably effect the development of seeds on the spo ear. Further, the spo effect enhances the per se yield of the parent inbred by increasing the size and kernel number at the tip of the ear.

DETAILED DESCRIPTION OF A PREFERRED EMBODIMENT

As used herein, terms employed to define the shapes of the ears are defined as follows:

1) Spo ear: one which has a decidedly "spoon shape" at the tip or expanded ear tip as judged by increased kernel rows at the tip versus the base. Spo ears have a wider ear tip than base and an increased kernel row number. Some spo ears, for example, may have 24 to 36 or more useful kernel rows at the tip of the ear while having 14-18 kernel rows at the base of the ear. Spo ears may be bulbous. Under the outer pericarp layer of a spoon shaped ear tip one may often find a hollow area which is compressed on each side to form the spoon or "spo" effect, although this is not always the case. Some spo ears may be 10 centimeters wide at the tip while only half that width at the base of the ear. The spoon shaped or bulbous ear tip is expressed in the highly inbred plant. When spoon eared inbred plants are crossed from different parental populations, the flat ear spoon trait is most often modified into a round or off round large bulb with higher tissue or seed yield at the tip versus non-bulbed plants. This rounding or bulbing permits normal machine harvesting and shelling without the losses which may occur with flatter ear breakage.

2) Bifurcate or split ear tip: defines an ear with one or more deep indentations into the tip of the ear usually containing eight or more kernel rows per arm of the bifurcation.

3) Spo-bif ears: defines and ear having large spoon shaped tips with visible indentations into the spoon.

4) Bif: As used herein, "bif" is defined as a field plot name as well as a descriptor for indented ears. As a term employed herein, it has nothing to do with any prior use of "bif" in any other context in genetics or biological chemistry.

Applicant groups all corn ears with increased kernel rows at the tip whether spoon or split or spo-bif or bulbous under the general term "spo".

In 1985, self-pollination of a corn line was accomplished by way of a three-way cross of Mo 17 and P3906 to produce an F2 generation. Mo 17 seeds were obtained as pure breeding stock from Downing Foundation Seeds, in Ohio. P3906 was a commercial single cross hybrid used at the time by farmers desiring an early flowering hybrid. P3906 was purchased at a feed dealer.

Neither parent possessed spo or bifurcate ears. Each parent was grown before starting the research to assess its ear type. Little ear variation, except as to ear length and kernel row number was found in either parent. Both parents possessed nearly parallel sided ears except that those of P3906 were slightly more conical at the ear base than Mo 17. Mo 17 had mostly ears with 12 or 14 kernel rows of seed with very few 16 kernel row ears. P3906 had mostly 14 and 16 kernel row ears. The seed rows and individual harvests made from each generation of self-pollination of Mo 17 and P3906 were encoded as follows in Table 1 below through each generation of selfing:

TABLE 1

| Year | Plot or Line # | Generation |
|---|---|---|
| 1985 | Mo 17 × P3906 | F2 |
| 1986 | 86-65-8 row | F3 |
| 1987 | S.B 2-5 row | F4 |
| 1988 | 3M9-17-10, 17-12 ears | F5 |
| 1989 | G Plot: 3M9-17-10 self 12 | F6 |
| 1990 | 90-RII-137-139 ear bag-2 | F7 |
| 1991 | 91 Block self SE-1 | F8 |
| 1992 | 92 Bif-rows 2, 4, 8, 12 | F9 |
| 1993 | 93-92 Bif 12-2 | F10 (.93PHI Bif-8**) |
| 1994 | TX row78 ex93-92Bif 12-2 | F11 |
| 1995 | Blue Mounds - Spo row | F12 |
| 1996 | plot3 | F13 |
| 1997 | plot 3 male RHspo | F14 |

**In 1993, the segregation of traits in the progeny of Bif-8 was as follows:

TABLE 2

| Spo tip | 52.9% |
|---|---|
| Normal Ear | 47% |

The research proceeded with a self-pollinated plant from 92 Bif-12, designated 93-92Bif 12-2, grown in TX row 78, in 1994, due to better plant type. At the F6, F7 level of inbreeding, it was noted that several ears in the family made from Mo 17×3906 exhibited the "spo" trait. Seeds of one of these plants were propagated as the 1991 Block SE-1 self ear and then the 1992 Bif plot, rows 8 and 12 as indicated above. Twenty plants from SE-1, grown in 1991, were self-pollinated. The resulting ears on these plants were 40% normal tipped and 60% spo tipped (widened at the tip). An ear exhibiting a strong "spo" trait was selected from 92 Bif plot row 12 and propagated, in 1994 and 1995, and reselected. The 1995 field row yielded 24 spo ears and 7 normal ears. In 1996, the spo trait was 70% in occurrence, 400 hills were propagated as Ripp Hill ("RH") Plot 3 male.

Using only two of the best spo trait ears from 1996 for the 1997 planting, the 1997 harvest gave approximately 80% clearly spo-eared plants with some slight spo ears, slightly expanded at the tip but not fully expressing due to local environmental effects. The spo ears were then bulked from Ripp Hill plot 3 as an F12 near homozygous line and employed later for tests and breeding purposes as a spo maize inbred, 97 RippHill male (hereinafter "97RHspo"). The spo trait in the 97RHspo family was recessive. Some plants in largely spo populations had tassel vestiges, these plants where termed "scalped" tassel.

In our field preparations at generations F8-F12 it was necessary to plant more hills than normally needed to propagate during the inbreeding process to make certain that good pollen shed could be obtained to continue selection of other useful traits such as husk cover, pollen shed, and disease resistance, and the like.

In 2004, 97RHspo yielded approximately 60% spo-eared plants on average when grown in isolation in South Carolina, as opposed to prior work done in Wisconsin. The field was heat stressed which is believed to have had a role in the expression of "spo" in this family.

Testing the dominance of the spo trait from 97RHspo in a backcross test of normal ear by spo, crossed as (norm ear× spo)×spo, found the spo trait was recessive in the F1 generation and gave a 50% expression in backcross-1 as if it were a single recessive genetic trait.

In 1997, we examined a hybrid of two "spo" family plants. The female was partially spo condition from a different family, VM 017, than the male, and the male was a precursor to 97RHspo. The hybrid row ears yielded as follows as grown in a 12 hill row:

TABLE 3

|  | Ounces dry weight seed per plant |
|---|---|
| Hybrid plant with normal ears: | 4.33 |
| Hybrid plant with spo ears: | 5.36 |

It was noted that the flat spo of the inbred was now altered in the spo×spo hybrid to an enlarged more round ear tip with normal underlying tissue, generally a greater kernel number at the distal tip than normal ears. Kernel rows numbering 18-32 on average were produced per ear at the tip, but as many as 48 small ear tip kernel rows would also develop on some plants. The base of the ears had generally 14-16 kernel rows. The hybrid spo×spo plant possessed cob tissue which had been filled-in by the effect heterosis had on the center and periphery tissue of the cob. This generally formed a more firm ear than the more fragile tip of the spo inbred parent.

This practical control of the hybrid ear tip tissue and increase in kernel number in each hybrid spo ear homozygous for spo is a highly advantageous development over the prior art. Generally, plant breeders discard any misshapen or off type ear during their selection process. For the present invention, it was necessary to define spo type inbreds to establish the new method of production.

Geneticists typically discard misshapen or odd ears as an environmental quirk which never breeds true. Since the genetic control elements are recessive, breeders would not see spo ears in the normal inbred or hybrid×spo test crosses. Because the discovered spo trait is recessive, it is not easily detected in commercial F1 test crosses involving common maize parents. The discovery mechanism to develop spo eared plants from a divergent cross of normal eared inbreds (standard maize parents) also has not been employed to produce such inbred parents as described herein as "spo" or ears with an expanded ear tip and increased ear tip kernel row numbers.

Now, useful hybrid corn production using spo×spo is possible since the enlarged ears shelled easily with a mechanical sheller. It was probable that the heterozygous genes in the parent hybrids for cob traits other than "spo" caused the plant tissues around the spo form to fill in and assume a fully expanded round to bulb like or spindle-like ear at the hybrid ear tip. There was a seed yield advantage in the spo hybrid versus non-spo hybrids from the same cross. The spo hybrid appeared suited to the commercial seed corn sheller with minimal loss expectation. Most flatten parent ear tips of the parent inbreds were generally modified in the hybrid form to stronger ears supported by firm underlying cob tissue. The flat tipped spo or slightly enlarged inbred parent ear, in contrast, may have a considerable weakness at the tip which, if projected into the hybrid, might preclude its use and promote mechanical harvest losses. Thus, heterozygotes at genetic loci other than spo appear to fill in the ear and overcome the spo parent's inbred ear tip weakness where it occurs. However, many spo ears are not flat and may just be enlarged bulb shaped ears as inbreds at the tip of the ear.

Prior to the research disclosed herein on spo and bif traits, and the making of inbreds from plants expressing these traits, breeders would have considered the spo ear trait a defect and discarded them. Thus, in the USA there are no commercially available spo inbred parent lines on the market and no hybrids of this type.

A second spo family was formed from normal ear inbred plants as follows in Table 4:

TABLE 4

| Year | Plot or Line # | Generation |
|---|---|---|
| 1984 | H99 × A632Ht |  |
| 1985 | H99 × A632Htx2 | F1 |
| 1986 | 86-56-1 | F2 |
| 1987 | STCO-I ear20 | F3 |
| 1988 | BX94 ear A3 | F4 |
| 1989 | Bulk Plot 2-62 | F5 |
| 1990 | C. Hill ear 017(spo ears present in plot) | F6 |
| 1991 | STCO-II @7/18 spo | F7 |
| 1992 | Bif plot #017-2 spo | F8 |
| 1993 | TX plot 199@8/10-1 spo | F9 |
| 1994 | 94 STCO-I spo | F10 |
| 1995 | PH-I | F10 |

H99 and A632Ht are common inbred parent lines employed in the corn seed industry. H99 is a public inbred from Purdue University. Many ears in the F3-F6 generations were spo and bif types. At the F6 stage plants from a single ear inter-pollinated by spo males was selected as F6 ear #017 (designated as VM 017). It was a normal tip dominant ear. The F6 ear VM 017 was grown, in 1991, as an F7 in a plot termed STCO-II, wherein the spo trait in its progeny was selected for increase as F8 through F10 generation. In the F10 plot grown in isolation, plants were selected against disease and insect damage, and for agronomic fitness. Plants were also selected for spo or bif trait, husk cover of the ear, and dry down. Twenty-four spo/bif ears were harvested and 25 normal ears at F10. These were taken to the laboratory where the following data was collected, as shown in Table 5:

TABLE 5

|  | Cm ear length | Grams dry seed/ear | Grams dry wt. cob/3 cm ear tip |
|---|---|---|---|
| Spo ear: | 14.7(1.3) | 61.5(17.4) | 1.27(0.49) |
| Normal ear (std dev.) | 13.7(2.0) | 57.8(18.1) | 1.07(0.59) |

In 2004, a plant was increased from 86-56-1 (H99×A632× 2S1). At the F9 stage in 2004, the spo trait was 70% occurrence. The genetic purity of the line as judged by the number of self pollinations was greater than 97%. Since the occurrence of spo was less than 100% at near purity, there may be slightly different degrees of penetrance of expression as effected by environmental or complementary elements of the corn genome.

In this family, the "spo" ears of a highly inbred population had a greater ear length, produced more dry seeds per ear, and had a greater dry weight of cob at the ear tip as would be expected from the spo shape of the ear. It is important to note that such an increase in dry weight of cob tissue at the tip of any maize ear has not been quantified in the past. This procedure employing ear tip tissue mass as a yield selection method is a new breeding method for maize.

Our result indicated that one value of a spo eared plant is per se seed yield increase of inbreds employed for parent seed production. Parent seeds are sold at much higher prices per unit weight than hybrid seed due to their proprietary nature and cost of production. Production of pure parent seeds must be done in isolated fields so that pollen contamination does not occur. Parent seed fields must be rogued free of "out crossed hybrid plants" before pollen shed. The high research cost leads to more value per bushel for parent seeds. Spo gene plants have expanded ear tips which vary slightly from family to family as to the tip width of the spo ear. However, the spo phenotype is easily distinguishable in the field as a visible marker at harvest. Thus, the spo effect may be employed as an inbred marker when used with other standard descriptors.

Other than the present invention, there has not been any prior spo inbreds based on Mo 17, A632 or H99 parents. Such phenotypic markers may improve the detection of patented varieties for determining infringement, as well as improving the enforcement ability of contracts between the trait proprietor and licensee, or federally regulated production.

One method of selection from generation to generation for developing a spo inbred is harvesting the ears, drying them, and then calculating the grams seed yield or grams dry cob yield per three centimeter tip of the ear and comparing it to a set portion of the ear base. This was done for 23 spo ears of 95PH-I with the following results, as shown in Table 6:

TABLE 6

| | |
|---|---|
| mean cob tip dry wt. = | 1.27 g, best plant 2.13 g |
| standard deviation = | 0.49 g |
| mean base cob wt. = | 3.31 g |
| standard deviation = | 0.54 g |
| avg ratio tip/base = | 0.38 g, best plant 0.60 g |

The ratio of tip to base weight for the spo population was on average 0.38 vs. 0.34 for normal ears in this family. When breeding for increased ear tip weight, plants with a higher cob tip to base weight ratio may be selected, which, in the above case, was a plant with a 2.13 g tip weight whose tip to base ratio was 0.60 g. Alternatively, plants simply with the highest tip weight per unit length may be selected. The tip is isolated by shelling the ears, placing the weighed seeds in numbered packets corresponding to the ear, and cutting the cob 3 centimeters back from ear tip with and weighing the 3 centimeter cut pieces. The plants with the best increase in weight of cob tip, or seed plus cob tip, are saved for propagation. Judgment must be employed by the breeder as to whether the enlarged ears are useful in a practical sense when compared to other traits of the plant such as having sufficient husk to cover the enlarged ear and sufficient disease resistance and the like. The selections procedures other than for "spo" traits have been well described.

As previously stated, ear VM 017 was isolated, in 1992, as a normal ear in a spo plot. It was heterozygous for the spo gene as we isolated spo plants from it when it was self-pollinated. Bif plot row 8 spo×VM 017 were also crossed in 1992, and the progeny tested, in 1993, for its hybrid effects. Bif row 8 was derived from Mo 17×P3906 as discussed above for Table 1.

The hybrid progeny yield test was conducted as follows: Commercial hybrid P3475 was planted in the field adjacent to the spo×spo hybrid. The experimental hybrids were planted in 96.5 cm wide rows at 15 hills per row and 23 centimeters apart within the row. A few ears were picked from replicate rows and dried and shelled. Their moisture was determined with a standard corn seed moisture meter and dry weights were then calculated. In two rows the spo and normal ears were segregated and shelled and dried separately. Normal ears appeared because one of the parents was not yet homozygous for spo (#017). Results are shown in Table 7.

TABLE 7

| Units mean dry seed weight in ounces per ear: | | |
|---|---|---|
| | Non-spo ear plants: | Spo-ear plants: |
| Bif-8 spo × 017 spo het | 4.6 | 5.9 |
| P3475 (row nearest above) | 6.5 | — |
| Bif-8 spo × 017 spo het | 3.8 | 6.0 |
| P3475 (rows nearest) | 6.6, 5.7 | — |

Within the experimental row the "spo" trait increased ear seed yield dramatically compared to "non-spo" eared plants, but not yet as high as commercial hybrid P3475, a later maturing plant. However, without any significant annual selection by yield testing prior to this first hybrid cross, the spo×spo cross approached the ear yield of P3475. The latter is a plant which represents many years of research by dozens of technicians and geneticists at Pioneer Hi-Bred Co.

Additionally, in 1983, the hybrid P3780 was purchased and the F2 seed from it planted. The sequence of plantings was as follows in Table 8:

TABLE 8

| Year | Backcross Female Line | Backcross spo Male |
|---|---|---|
| 1984 | F1 P3780 | F2 Mo 17 × 3906 |
| 1985 | F2 row 211 | made F3 Mo 17 × 3906 |
| 1986 | F3 row 88 ear 1 | made F4 86-65-8 |
| 1987 | F4 A1110-4 | madeF5 S.B2-5 |
| 1988 | F5 3M9-28 | made F6 3M9 |
| 1989 | | Plot G-3M9*** |
| 1990 | crossed by Bif-16 | 3M9-28 × Bif 16spo × 90 Bif-16spo |
| 1991 | | 3M9-28 × Bif-I6x2* × 91 (Bif-16S1)** |
| 1992 | | 3M9-28 × Bif-16x3* |

***Parent of Bif-16
**large spo ear tip employed as a male.
*1.27 cm split tip ear used as female in backcross.

In the above crosses, 3M9-28×Bif-16×2 had a 1.27 cm indented ear in a spo shape. Six ears of backcross-1 gave 4 spo ears, two of which had indented character. Thus, the increased tip tissue was expressing at a rate of 66% of ears in this small sample. The spo trait could be expressed easily in the backcross onto germplasm from P3780. This experiment, while tedious and taking several years to conduct, provided evidence that broader commercial germplasm could be used incorporating the spo trait as a genetic determinant to confer expanded ear tip phenotypes.

A typical indented ear of 3M928×Bif-16×3 was closely examined. It possessed a 3.4 cm indentation in a spo-shaped tip. One indentation or branch of the ear tip possessed 18 kernel rows of seed, the other 14 kernel rows. The base of the ear, taken a distance from the base tip, to the start of the expanded portion of the ear had 14 seed kernel rows. Twenty percent of the ear length was represented by the expanded "spo" structure.

In 1993, examination was done on a typical parent ear of Bif plot row 26 which showed spo character after five self pollinations of a backcross hybrid (Sp288×H99)H99. H99 was obtained from Downing Foundation Seed Co. Neither parent ear was spo in nature prior to the backcross. The dry spo ear was 14.5 cm long with a 6.0 cm spo length at the tip which was 4 cm wide. It was indented to give two shallow branches. The spo length was 41% of the ear length. The kernel row number at the tip was 32 for each branch vs. 24 at the base of the ear. The kernels were well developed and covered the branches entirely. From the 1992 harvest, we compared normal ears vs. full spo ears from several rows as to ear length, dry cob weight, weight of 5 cm base and 7 cm tip. The grams dry weight per centimeter of cob at the base and tip was calculated. Weights were after drying to a constant dry weight. The results are shown in Table 9.

TABLE 9

| pedigree# | ear type | ear length | g dry weight whole cob | g/cm @ base | g/cm @ tip |
|---|---|---|---|---|---|
| #017 | normal | 17.5 cm | 26.5 | 2..0 | 1.6 |
| #017 | spo | 17.5 cm | 28.9 | 1.4 | 1.9 |
| Bif 26/29 | normal | 13.3 | 18.9 | 2.3 | 0.7 |
| Bif 26/29 | spo | 14.6 | 29.5 | 3.0 | 1.7 |

All numbers were rounded to the nearest tenth unit.

The spo ears were generally heavier with a minimum of 9% increased ear tip weight of cob tissue. The whole cob weight of spo ears was 9-35% heavier than normal cobs in this observation. Other pedigrees were observed in which we segregated out spo ears vs. non-spo ears from each row. These gave the following results from a sample size of 3-6 ears per lot, as shown in Table 10.

TABLE 10

| Mean units ounces dry seed per ear | | |
|---|---|---|
| Plot Hybrid Code | Non-spo | Spo |
| Bif-11 × Bif-2 | 4.9 | 6.2 |
| Bif-29 × 19-2 | 5.0 | 6.5 |
| Bif-26 × 25-3 | 4.1/3.5 | 6.8/6.2 |
| Bif-12 × 19-1 | 5.1 | 6.7 |

100% spo ears in each row was not achieved in the above trials because at this stage of breeding both parents were not shedding pollen completely homozygous for the spo trait. However, it was apparent at harvest that the spo ears on hybrid plants gave advantage in seed yield and contributed to yield within the same pedigree row.

In 1993, three full set spo ears and three full set normal ears were harvested from the center of a row expressing both traits in the same pedigree. This was 3m9-28×Bif16×3×89Bulk2-101-102 lot 5. The goal was to see again if in the entire absence of any insect feeding, disease or silk cutting effects on the ear tip, how the ear seed yield compared. The closely observed data were as follows for three fully set ears as shown in Table 11:

TABLE 11

| Fully Set Hybrid Ear Data | | |
|---|---|---|
| | Normal Ear Tip | Spo Ear Tip |
| Mean whole ear weight | 199.9 g (19.3) | 266.8 g (24.9) |
| Mean seed weight/ear at pick | 164.3 g (17.0) | 222 g (16.0) |
| Mean seed dry wt. (standard deviation) | 126.4 g (8.3) | 179.6 g (10.9) |

The spo trait gave a greater seed yield. It was concluded that the spo trait was a means of increasing corn seed yield and an adjunct to standard breeding of maize. We concluded that spo trait in an inbred can be selected or derived from non-spo and non-furcate heterozygous parents by crossing hybrids, synthetic populations and inbreds of different origin and selecting the progeny for increased ear tip weight and size. The spo trait may be fixed during inbreeding as a novel heritable determinant derived from the exchange of or mutation of DNA which occur naturally, i.e. such as crossing over of chromosomes from normal eared plants. Regardless of its molecular origin, the fixation of the spo trait was evidenced by the greater percentage occurrence of spo ears as a result of the selection process and its appearance in hybrids.

An exemplary family of spo inbreds was formed as follows in Table 12:

TABLE 12

| Year | Plot | Generation |
|---|---|---|
| 1985 | back cross of H99 onto an H99 hybrid (Sp288) was completed in an isolated field | |
| 1986 | | F2 |
| 1987 | row 7112 | F3 |
| 1988 | row PP 11|7-5 | F4 |
| 1989 | row Bulk 2-101-102 spo | F5 |
| 1992 | row Bif-26 spo | F6 |
| 1993 | row Block@code20 | F7 |
| 1994 | row Pump House I male spo | F8 |
| 1996 | plot 11A male spo | F9 |
| 1997 | location 6 of 96-11A spo | F10 |
| 1999 | farm II-c | F11 |

This family produced excellent spo ears which are termed "11Aspo." Sixteen 11A male spo ears were dried for 3 days at 125° F. Then their dry length was determined as 13.2 cm (1.5). Ten ears were compared for their seed yield capacity as kernel row numbers at the base of the cob (1 cm above butt of ear) versus kernel rows at 8-9 cm above the base. The results were significant. Average kernel row number at the base 18.6 (2.3) and at the 8-9 cm level of the ear 22.7 (1.8). For the population examined, the seed rows increased on the average by 4.1 toward the tip of the ear versus 1 cm for the base. This is the reason for a higher seed yield from our innovation in an inbred parent. The genetic results of this are discussed below.

Commercial hybrid RK76 was backcrossed by "11Aspo" and the progeny showed 23 spo ears and 24 normal ears (1:1 segregation). The one to one spo to normal ratio in the backcross progeny indicated a high probability of a single recessive gene or very closely linked recessive genes inherited together are responsible for the spo trait. (RK76×spo)× spo was crossed by (P3475×spo)spo and the F2 progeny gave 94 spo eared plants and 64 normal ears. (DeKaib hybrid 512× 11Aspo)11Aspo showed 7 spo and 11 non-spo in the backcross progeny. In spo family 11Aspo, new spo inbreds were recovered by backcrossing P3475×11A and self-pollinating the backcross with selection for spo, disease resistance and good husk cover of the ear. This family is termed VM179spo2000.

In 2004, VM179spo2000 was grown to produce S4 ears (self four) on S3 plants of P3475×11A×2. The S3 plants bore 69% spo ears of a well formed nature on plants with excellent agronomic traits. The plants had 11 tassel branches, red cobs and a mean stalk strength by crushing in a Carver press of 676#.

It has been shown herein that 11Aspo can be backcrossed onto two widely employed hybrids P3475 and RK60 to derive spo lines from widely employed hybrid germplasm; and, selfing Mo 17× hybrid P3906 to derive spo lines. In the case of P3475 the backcross by 11Aspo showed the trait can be rapidly selected to modify the tip contribution of the ear to ear weight and yield.

The spo trait once isolated can be transferred to many inbreds for their improvement in per se yield and in hybrid crosses, including but not limited to, A554, A632Ht, A632, A641, A634, A619, A619Ht, A670, A672, B14, B14A, B37, B68, B88, B75, B76, B79, B73, B83, B84, B85, B87, B88, B52, C103, C123, CB59G, CD1, CD2, C123, CG9, CG11, CG12, CG13, CG14, CG15, CG17, CG18, CG20, CG576-3, CH581-13, CH591-23, CH592, CH593, CH611, CH646, CH661-17, CH665-1, CH671 and derivatives; CH711, CH753-4, CK24, CK69, CM105, C0109, C0150, C0220, CO252, CQ169, CQ173, CQ187, CQ188, CQ193, CQ196, CQ206, CQ213, CQ214, WF9, W23, CQ704, DF11, DF13, DF21Ht, F488, F578, FR3, FR22, FR27rhm, FR807, FR1130, FR1193, FR809, FR810, GT210wx, H99, H94, H95, H108, H109, H115, H125, Hi31, Hi35, K201, Ky128, LH53, LH74, LH55, LH92, LH98, LH106, LHE137, LH143, LH146, Mo17, Mo40, Mo42, Mo401, Mp488, Mp490, Mp701, Mp703, MS24, MS71, MS92, MS74, MS132, MS214, N28, N31, NC230, NC250, ND230, ND246, ND255, ND256, ND101, ND468, ND481, NY821, Oh43, Oh45, Oh51, Oh422, OH561, Pa91, Pa347, Pa409, Pa878, R177, R806, R182, RB73, RB73Htrhm, SC01, SC343, SD5, SD10, SD22, SD37, SDp288, SDp310, SDp312, SDp84, SDp309, T232, T250, Tx2783, Va26, Va35, VA21, VA43, Va59, Va95, Va96, Va98, W182B, W540, W117, W64A, W64Arms, W454. Desired traits transferred through the backcrossing process that can be combined with the recessive trait for expanded ear tip include, but are not limited to, herbicide resistance, insect resistance, resistance to bacterial disease, resistance to fungal disease, resistance to viral disease, modified fatty acid, modified carbohydrate metabolism, decreased phytate content, male sterility and corn endosperm with improved nutritional quality. For a further discussion of backcrossing methods, refer to U.S. Pat. No. 6,914,177, incorporated fully herein by reference.

Certain synthetics may also be converted to spo trait such as "Iowa stiff stalk synthetic" from which have been derived many inbred lines in the past through test crossing. The above inbreds may have resistance genes for northern leaf blight, corn smuts, wind and fungal induced lodging, corn rust, downy mildew, anthracnose, southern leaf blight, and grey leaf spot added by various backcross procedures without impairing the spo trait.

Additionally, the advent of new molecular biological techniques has allowed the isolation and characterization of genetic elements with specific functions, such as encoding specific protein products. Scientists in the field of plant biology have developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes". Over the last fifteen to twenty years several methods for producing transgenic plants have been developed, and the present invention, in particular embodiments, also relates to transformed versions of the inbred maize lines expressing the spo trait, as well as hybrid combinations thereof, as discussed above. A genetic trait which has been engineered into a particular maize plant using transformation techniques, could be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation then the transgenic plants could be crossed to a different inbred in order to produce a transgenic hybrid maize plant. Various genetic elements can be introduced into the plant genome using transformation. These elements include but are not limited to genes; coding sequences; inducible, constitutive, and tissue specific promoters; enhancing sequences; and signal and targeting sequences. See the traits, genes and transforming methods listed in U.S. Pat. No. 6,118,055, which is herein incorporated fully by reference.

As discussed above relating to desired traits transferred through the backcrossing process, such desired traits may include, in combination with the recessive trait for expanded ear tip, herbicide resistance, insect resistance, resistance to bacterial disease, resistance to fungal disease, resistance to viral disease, modified fatty acid, modified carbohydrate metabolism, decreased phytate content, male sterility and corn endosperm with improved nutritional quality. For a further discussion of plant transformation methods well known to those skilled in the art, refer to U.S. Pat. No. 6,914,177, as well as U.S. Pat. No. 6,642,441 incorporated fully herein by reference.

Accordingly, a preferred method for enhancing hybrid yield is to isolate by the process herein the spo trait in an inbred, then backcross the spo inbred to commercially useful inbred parents to make a spo hybrid, example B73spo×Mo17 spo, which is locally adapted.

It is clear that a means for increasing the yield of corn inbred parents and hybrids by isolation of a recessive gene for an expanded ear tip is disclosed. Using this "spo" trait in single cross and backcross hybrids among genetically diverse inbred parents, breeders can achieve increased yield. The parent hybrids and inbreds need not express the expanded ear tip character at the outset of the selection crossing program. The character may be selected from naturally segregating normal eared populations such as a synthetic or synthetic× inbred population. These general processes of gene modification are already known as inherent in the maize plant such as chromosome crossing over, mutation, deletion, mutator genes and epistasis of closely linked genes. The prior art of maize structure and its genetics reports on many kinds of distorted and variant ears, the prior art does not teach how to employ and isolate useful variations for a hybrid and inbred yield improvement program. Thus, the present invention is a significant advantage over the prior art teachings.

Hybrids made by crossing "spo heterozygotes"בnear pure spo" inbreds as well as "near pure spo homozygotes"בnear pure spo homozygotes" showed the trait is manageable in the hybrid to increase ear tip yield. As demonstrated, the spo trait can be developed from common inbreds and their hybrids such as the inbreds A632, Sp288, H99, and Mo17, and from commercially available hybrid germplasm as exemplified by DeKalb 512, P3906, and P3475. The spo trait is likely a single locus which has fair penetrance in all hybrids where it is homozygous in the parents as derived by the disclosed method of selection. Results from crossing spo×spo and spo× non-spo inbreds would be expected as follows, as shown in Table 13:

TABLE 13

HYBRID EAR TIP RESULTS

| Female parent | Male Parent | |
| --- | --- | --- |
| | 1. Non-Spo | 2. Expanded or Spo |
| 1. Non-spo or normal tip | normal tip | normal tip |
| 2. spo parent or expanded tip | normal tip | increased spo or expanded tip |

In the breeding of commercial maize today, the inbred ears required to obtain the category spo×spo hybrid in Table 13, would be discarded as deformed or abnormal. However, according to the methods of the present invention, the advantage of increased seed yield from an expanded ear tip resulting from homozygous recessive genes in a hybrid is now a reality.

Maize inbred and hybrid plants with parallel sided normal ears or slightly conical sided normal ears may be crossed in the first stage of the process discussed herein. Such crosses may be inbred×inbred (A); or hybrid single, double or three-way cross×inbred (B); synthetic population×inbred or hybrid (C); inbred backcross (D); or hybrid by hybrid (E); each of these crosses forms the population to be selected during inbreeding. These crosses and types of hybrids are described in the art by such texts as Principles of Plant Breeding (R. W. Allard) and Hybridization of Crops Plants (by Fehr and Hadley), and various articles by Am. Soc. of Agronomy.

The products of each of the above crosses is designated herein by standard breeding terminology as an "F1" or first filial generation. The F1 generation seeds from a random sample of ten to five-hundred in number are planted in hills and the resulting plants are self-pollinated ("selfed") to form F2 generation seed on the F1 sporophyte. At this stage F2 seeds are collected from plants with regards to disease resistance, husk cover, flowering time and pollen shed in a normal fashion consistent with the art of maize breeding. No attention need be paid to the ear traits in the F2 harvest. These seeds are planted ear-to-row to provide F3 seeds on the F2 sporophytes. The F2 may be planted in from 1-40 rows since the parent is still largely heterozygous. One should recall that the cob of the corn ear is the F2 on which F3 seeds are formed by pollination. The best appearing F2 plants from the standpoint of agronomic traits such as growth, disease resistance, pollen shed, and the like are again selected as single ears. F3 seeds are collected and seeds planted in a few rows from each ear wherein 25 or more plants will result from each ear, or in isolation as a block of hills totaling 250-500 hills/block (which will depend in part on the amount of seed available). The seeds from different F3 plants should not be mixed. Plants in this large row or block may be self-pollinated by hand, sib pollinated by hand or allowed to inter-pollinate openly as long as no other pollen is available as a contaminate. At this stage the F4 seeds are produced. The ears bearing the F4 seeds are carefully screened for ears having one or more of the following traits:

1. a tendency toward a split tip at the distal end of the cob;

2. an enlarged cob toward the tip with more kernel rows at the mid-part of the ear and beyond toward the tip than at the base. For example, if an ear has 16 kernel rows at the base and 20 kernel rows appearing at the mid-portion of the ear and beyond, this would be a key finding and that the ear should be saved for propagation as an F4 sporophyte;

3. single ears with a greater weight of tissue (mass) toward the tip of the ear, or more harvestable seed in number from the distal portion of the cob than the lower portion of the ear using a few centimeters in which to judge the seed set per cob centimeter length, and more florets by number in the distal upper half or so of the ear than the base. Ideally ears can be selected which show a decided expansion of the cob in the distal 50% of the ear which bears seed; and, 4. an ear with a transition "zone" of seeds (florets) crammed apparently randomly together into 18-24 kernel rows with lesser kernel row numbers found below the transition zone toward the base of the cob.

Ears which appear normal in kernel row number and floret geometry along the length of the ear and which would normally be selected for their size, weight and good appearance, such as straight kernel rows, ear length and narrowing uniform symmetry toward the tip are discarded, or held as backcross females for later, in favor of ears meeting one or more of the above criteria (1-4).

If no ears display the desired selection criteria described in items 1-4 above at the F3 or F4 stage of inbreeding, several (20 or more ears) from good plants are carried forward to the F5, F6, or F7 generations and the cycle of selection is repeated again. One should carry forward more seed for planting and selection at the F5-F7 generations than in the F2-F4, preferably 500 or more hills should be planted each year in the advanced generations. It is not unusual in some populations that the phenotypic trait of expanded ear tip as describe herein may not be isolated as a selectable phenotype on an agronomically fit plant until F6 or beyond. This means several years effort before a useful result is seen or obtained. For example, in the development of line 97RHspo the spo trait was not identifed until ear SE-1 was found in an F7 population of a cross made seven generations earlier involving Mo17 crossed by a hybrid.

Once the trait of an expanded ear or an ear with greater seed number toward the tip than at the base (as a result of greater kernel row number/floret number) has been isolated, it is carried forward to assess the heritability of the trait in subsequent generations of inbreeding. Ear to row breeding of the plants showing the desired trait is practiced until the percentage expression of the trait becomes fixed or expresses at a high percentage in the progeny. At each cycle of selection "normal" ears with no change in kernel row number toward the tip or a declining kernel row number toward the tip are discarded in favor of ears with the increased tissue mass and/or floret number toward the distal portion of the ear as compared to the base of the ear. At apparent fixation of the ear type in a high percentage of the plants the seeds from sister ears may be bulked and considered a true breeding population or inbred line. Since this occurs generally at F6 and beyond the plants' other physical traits have little variance in appearance.

Importantly, the expression of the spo trait of an expanded ear tip and ear tip seed yield may vary somewhat from year to year depending on the environment. Generally, 40%-100% of the inbred plants selected for the increased ear seed yield toward the tip will express the trait at a highly homozygous stage year after year on essentially identical inbred plants. This percentage expression, also known as penetrance in genetic terms, is effected by modifier genes and the enviornment from the different families in which the inbred may have been derived. Such modifier genes might for example be turned on and off by alterations in the environment. The line 11Aspo inbred has a high percentage penetrance, approximately 90% or greater, while the line 97RHspo has a lower penetrance. In the inbreeding process of the present invention, high penetrance or expression is desired. The spo trait is recessive but its penetrance is such that in hybrids made from spo eared plants, a significant percentage of the hybrid made will have greater seed yield contribution toward the tip of the ear as a result of our breeding method employed to make the inbred. In each hybrid cross made from spo inbreds made by this process, ears with the spo trait may be found in the hybrid F1 progeny rows. These hybrid spo ears have increased floret number at distal portion of the ear, many have an expanded cob which may be spindle shaped.

Thus, the spo inbred plants, as termed herein can be made by essentially discarding normal eared maize plants during inbreeding procedures to produce hybrids with expanded cobs and increased kernel numbers toward the tip of the ear.

Plant Descriptions:

97RHspo: A maize inbred derived from the pollination of Mo17 (Missouri 17 USDA release)×hybrid pollen from P3906. At purity the plant height averages 139 cm with a variance of 14 cm. The leaf number per plant is generally twelve (12) rarely ten or 14. By leaf counts the mean number was 11.4 (standard deviation 1.8). Leaves are wide and upright with an average angle to the upper stalk of 15-16 degrees. Ear node height average is 39 cm above the ground. Leaf length is 42.3 (standard deviation 1.5) vs. 59-60 for the standard inbred H99 grown in the same field. Tassel branches average 5 per plant but may be 3-7 with over 50% of the plants with 5 branches and never 10-14 branches/tassel. The anthers are PMS 702 pink-red. Cobs are red. The third leaf down from the tassel (tassel-3) has a mean width of 8.0 cm at a distance of 20 cm from the stalk (standard dev. 1.3 cm) At 30 cm from the stalk the same leaf has a mean width of 5.1 cm (standard dev. 1.6). This decrease in leaf width prescribes a sharply pointed leaf with upright angle. In contrast, H99 inbred (Purdue University-USDA release) has a width of 7.5 and 7.4 cm at these respective distances. 97RHspo has a mean distance between the ligule of the top leaf and the second leaf of 3.9 cm (3.87 rounded) while for the standard inbred H99 this distance is 7.3 cm (standard dev. 1.1). Many plants appears to have the top leaf and the second leaf arising near to or from the same node because the ligules oppose one another at the top leaves. 97RHspo contains a recessive determinant for ear shape modification which has an average penetrance of approximately 60% in the phenotype. This determinant causes the ear to have more kernel rows further from the base of the ear than at the base, e.g. 8-10 cm from the base. The length of the dry ear is between 10-14.5 cm with 14-16 kernel rows appearing at the base of the female spike or ear and greater kernel rows may occur at 9-10 cm from the base of the female spike in the majority of plants. A transition zone from lower to higher kernel row numbers occurs generally 5-7 cm from the base of the ear. The tip of the dry ear distal from the stalk generally has a flattened appearance in approximately 60% of the plants. The width of the ear at its widest point is 4-5 cm freshly harvested, and a thickness of 3.0-3.6 cm wide in the dry state. The kernels are slightly elongate if shelled from the area of the ear with the highest kernel row number and become more rounded if shelled from the extreme base or tip of the ear. The kernels lack specific distinguishing features. The kernels have a yellow cap 1-2 mm in thickness on a slightly darker yellow base.

Prior to pollination the ear habit in the field is to show a wide yellow silk brush which forms when the wider ear structure pushes the husk aside. The silk is pale yellow and not particularly distinguishing. Under average growing conditions in the southern United States, 97RHspo is 3-4 days earlier on average than H99 by contrast.

The plants have a high degree of resistance to such diseases as northern and southern leaf blight and northern corn rust. Looking down a row one sees an upright dark green plant with large sharp pointed leaves at the top of the plant and uniform tassels with limited spike number. The ears have abundant silk and a widish appearance at the tip due to the underlying enlarged cob structure.

Plant 11Aspo: Plant 11Aspo is from a midwestern hybrid maize plant Sp288×H99 backcrossed by H99. The mean plant height of 11Aspo is 148 cm. Leaf number is 12-14 per plant with a mean leaf number of 12.4. Anthers are always yellow. Tassels have a mean of 7.3 branches but some may have 4 or as high as 14. Plants are 3-4 days earlier flowering than H99. The mean leaf angle at the tassel-3 leaf is generally 27 degrees to the stalk (standard dev. 5.4) with a few at 20 or 30 degrees. Ear height is 54 cm from the ground to the ear bearing node. Leaf length at the tassel-3 leaf is 39 cm and about 20 cm less than H99 by contrast. At 20 cm from the stalk the leaf width for the tassel-3 leaf is 6.6 (standard dev.1.3) cm which is 20-25% narrower than H99. At 30 cm from the stalk the tassel-3 leaf is 4.6 (standard dev. 1.4) cm wide and 38% less than H99. The distance from the lowest anther bearing tassel spike to the top leaf is 4.6 cm (standard dev. 0.8) which is very short compared to H99 at 7.3 (standard dev. 1.1).

Ears of 11Aspo have a red cob and on average 18.6 kernel rows (std. dev. 2.3) at the cob base. At 8-9 centimeters from the base ears have 27.7 kernel rows (1.8 std. dev.). A few ears may show as many as eight added kernel rows at the widest portion of the ear vs. the base of the ear. Greater than 90% of the ears of 11Aspo will have more kernel rows at half way or just over half way up the cob than at the base of the cob. This gives the whole ear an expanded appearance and, as discussed herein, is termed the spo effect.

A fully set dry ear is 12-15 cm long (mean 13 cm), 4.5-5.5 cm wide at a distance of 8-9 cm from its base and 3.5-4 cm thick, giving the whole ear a slightly flattened appearance toward its tip. Kernel rows at the ear base are typically 18-20 and 24-32 at the widest point. The kernels are dented, yellow and variable in shape. Those kernels harvested from the widest part of the ear may be 4-5 sided.

A comparison of 11Aspo, 97Rhspo and H99 is provided in Table 14.

TABLE 14

| Trait or Property of the Maize | Inbred 11Aspo | Inbred 97RHspo | Commercial inbred H99 | Comment: |
|---|---|---|---|---|
| Plant type: 1. sweet; 2 dent; 3 flint | 2 | 2 | 2 | |
| Days to maturity as black layer in S. Carolina | 90-93 | 88-92 | 96-100 | 110 days in Midwest for H99 |
| Centimeters from ground to tassel tip | 148.2(30)<br>N = 15 | 139.1(13.9)<br>N = 30 | 166(9.3)<br>N = 14 | |
| Centimeters to top ear bearing node | 54.4(15.3)<br>N = 8 | 39.0(8.5)<br>N = 32 | 61.9(4.0)<br>N = 14 | |
| Percentage tillered plants | <3 | <3 | | |

TABLE 14-continued

| Trait or Property of the Maize | Inbred 11Aspo | Inbred 97RHspo | Commercial inbred H99 | Comment: |
|---|---|---|---|---|
| Centimeters from lowest anther bearing spike to top leaf ligule | 4.6(0.8) N = 6 | 3.9 N = 32 | 7.3(1.1) N = 16 | |
| Percentage silked ears/plant | 1.63 N = 30 | 1.85 N = 30 | 2.0 N = 30 | |
| Ears setting seed per plant av. conditions | 1 | 1 | 1 | |
| Stalk color 30 days after pollen shed 1. above ear 2 lower stalk | 1. PMS 382 with a few to PMS375 2. PMS377 | 1. PMS 377 2. PMS 382 | 1. PMS 382 2. PMS 370 | |
| Silk color: 1. yellow - green PMS380; 2. pale green PMS374, slight pink may occur on a few ends <2% | 1 | 2 | 1 | |
| Width of exposed silk brush just after pollen shed: 1 = narrow 0.5-2 cm.; 2 = avg 2-3 cm 3+ wide many 3 to 6 cm wide | 3 | 3 | 2 | This feature is very distinguishing for spo maize |
| Tassel branches | 7.3(4.4) N = 8 | 4.6(1.7) N = 40 | 8.6(3.6) N = 16 | |
| Centimeters tassel length | 28.3(2.2) N = 16 | 31.2(3.4) N = 22 | Not noted | |
| Anther color: 1 = PMS 386 2 = PMS 702 deep pink-red | 1 | 2 | 1 | |
| Kernel row number @ 1-2 cm. from ear base | 18.6(2.3) N = 10 | 15(1.7) N = 20 | 13.6(1.2) N = 14 | |
| Median Kernel rows @ ear base | 18 | 16 | 14 | |
| Kernel row number at 8-9 cm. from ear base | 22.7(2.3) range of 24-32 | 17.9(2.2) | 12.9(1.0) | H99 like normal corn declines in kernel row number toward tip of the ear |
| Percentage field expression of wide ear tip | 90 +/− 10 | 60 +/− 10 | 0 | Penetrance of expression can vary somewhat with environment from year to year. |
| Cob color | red | red | white | |
| Seed color | Crown of kernel is yellow 2x base of kernel is MPS1162X | Whole ear aspect before shelling is yellow PMS 803 which is seed cap color | n.a. | |
| Seed shape | L = 9.5 mm (1.2) W = 5.4 mm (0.7 N = 25 | L = 7.5 mm(0.6) W = 7.1 mm(0.8) N = 25 | n.a. | |
| Gms. 100 kernel weight @% moisture | 20.3@ 0% moisture | 21.91 @ 5% moisture | n.a | |
| Starch type: 1. sweet 2. waxy 3. normal | 3 | 3 | 3 | |
| Leaf traits: cm. length | 39.1(4.1) N = 18 | 42.3(1.5) N = 22 | 59.7(2.3) N = 20 | |
| Leaf trait: cm width@ 20 cm from base; Cm width @30 cm from base | 6.6(1.3) 4.6(1.4) N = 17 | 8.0(1.3) 5.1(1.6) N = row of 15. | 7.5(2.0) 7.4(0.4) N = row of 15 | |
| Adaxial angle of leaf to stalk for tassel-3 leaf | 26.6 (5.4) N = 16 | 15.8(4.0) N = 24 | 24(1.4) N = 8 | |
| Percentage of plants with the ligules of top two leaves located at same point on stalk(appearing fused) | 0 N = 27 | 58 N = 53 | 0 N = 30 | |
| Disease resistance profile 5 = high resistance | | | | |

TABLE 14-continued

| Trait or Property of the Maize | Inbred 11Aspo | Inbred 97RHspo | Commercial inbred H99 | Comment: |
|---|---|---|---|---|
| 0 = nil resistance | | | | |
| Northern corn rust | 5 | 5 | 5 | |
| Northern corn blight | 5 | 5 | 5 | |
| Fusarium kernel rot | 4 | 1.5 | 4 | |
| Percentage spo ear expression | 96.0 | 48.7 | 0.0 | |
| Percentaqe decline in leaf width between 20 and 30 cm. | 30.4 | 36.3 | 2.4 | H99 is a more parallel sided leaf |

"N" indicates the number of plants observed
Numbers in parenthetical indicate standard deviation A deposit of the Fairview Industries, Inc. inbred corn seed 11Aspo and 97RHspo disclosed above and/or cited in the appended claims have been made with the American Type Culture Collection (ATCC), 10801 University Boulevard, Manassas, Va. 20110-2209. The date of deposit for 11Aspo was Sep. 16, 2005, and the date of deposit for 97RHspo was Sep. 20, 2005. The deposit of 2,500 seeds for both 11Aspo and 97RHspo were taken from the same deposits maintained by Fairview Industries, Inc., 233 East Main Street, Pendleton, S.C. 29670, since prior to the filing date of this application. Access to these deposits will be made available during the pendency of this application to persons determined by the Commissioner of Patent and Trademarks to be entitled thereto under 37 CFR 1.14 and 35 USC 122. Upon allowance of any claims in this application, all restriction on the availability to the public of the inbred will be irrevocably removed by affording access to a deposit of at least 2,500 seeds of the same inbred lines with the American Type Culture Collection (ATCC), 10801 University Boulevard, Manassas, Va. 20110. The deposit is intended to meet all of the requirements of 37 CFR § 1.801-1.809. The ATCC accession number for 11Aspo is PTA-6978. The ATCC accession number for 97RHspo is PTA-6982. The deposit will be maintained in the depository for a period of thirty years, or five years after the last request, or for the effective life of the patent, whichever is longer, and will be replaced as necessary during that period.

What is claimed is:

1. A method for producing hybrid corn seed comprising: crossing a first maize plant with a second maize plant wherein at least one of said maize plants is selected from the group consisting of inbred line 11Aspo, a representative sample of seed having been deposited under ATCC Accession No. PTA-6978 and inbred line 97RHspo, a representative sample of seed having been deposited under ATCC Accession No. PTA-6982, comprising a genetic determinant which confers an expanded ear tip phenotype, said genetic determinant is transferred to the hybrid seed corn as a recessive genetic determinant.

2. The method of claim 1 wherein said recessive genetic determinant is transferred to said hybrid corn seed as a single recessive gene.

3. The method of claim 1 further comprising backcrossing the maize plant carrying said recessive genetic determinant with a hybrid maize plant grown from the resultant hybrid corn seed.

4. A hybrid corn seed produced by the method of claim 1.

5. The method of claim 1 wherein said first maize plant is selected from the group consisting of A554, A632Ht, A632, A641, A634, A619, A619Ht, A670, A672, B14, B14A, B37, B68, B88, B75, B76, B79, B73, B83, B84, B85, B87, B88, B52, C103, C123, CB59G, CD1, CD2, C123, CG9, CG11, CG12, CG13, G14, CG15, CG17, CG18, CG20, CG576-3, CH581-13, CH591-23, CH592, CH593, CH611, CH646, CH661-17, CH665-1, CH671, CH711, CH753-4, CK24, CK69, CM105, C0109, C0150, C0220, CO252, CQ169, CQ173, CQ187, CQ188, CQ193, CQ196, CQ206, CQ213, CQ214, WF9, W23, CQ704, DF11, DF13, DF21Ht, F488, F578, FR3, FR22, FR27rhm, FR807, FR1130, FR1193, FR809, FR810, GT210wx, H99, H94, H95, H108, H109, H115, H125, Hi31, Hi35, K201, Ky128, LH53, LH74, LH55, LH92, LH98, LH106, LHE137, LH143, LH146, Mo17, Mo40, Mo42, Mo401, Mp488, Mp490, Mp701, Mp703, MS24, MS71, MS92, MS74, MS132, MS214, N28, N31, NC230, NC250, ND230, ND246, ND255, ND256, ND101, ND468, ND481, NY821, Oh43, Oh45, Oh51, Oh422, OH561, Pa 91, Pa347, Pa409, Pa878, R177, R806, R182, RB73, RB73Htrhm, SC401, SC343, SD5, SD10, SD22, SD37, SDp288, SDp310, SDp312, SDp84, SDp309, T232, T250, Tx2783, Va26, Va35, VA21, VA43, Va59, Va95, Va96, Va98, W182B, W540, W117, W64A, W64Arms, W454, and wherein said second maize plant is selected from the group consisting of inbred line 11Aspo, a representative sample of seed having been deposited under ATCC Accession No. PTA-6978 and inbred line 97RHspo, a representative sample of seed having been deposited under ATCC Accession No. PTA-6982.

6. A method for producing corn seed, said method comprising:
pollinating a maize plant selected from the group consisting of inbred line 11Aspo, a representative sample of seed having been deposited under ATCC Accession No. PTA-6978 and inbred line 97RHspo, a representative sample of seed having been deposited under ATCC Accession No. PTA-6982 with pollen from another maize plant, wherein at least 5% of the maize plants grown from the resultant seed possess a single recessive genetic determinant which confers an expanded ear tip phenotype.

7. A corn seed produced by the method of claim 6.

8. A maize plant grown from the corn seed of claim 7.

9. A method for producing inbred corn seed comprising a genetic determinant which confers an expanded ear tip phenotype which is transmitted to progeny as a single recessive gene, said method comprising inbreeding a corn plant selected from the group consisting of inbred line 11Aspo, a representative sample of seed having been deposited under ATCC Accession No. PTA-6978 and inbred line 97RHspo, a representative sample of seed having been deposited under ATCC Accession No. PTA-6982.

10. A corn seed produced by the method of claim 9.

11. An inbred maize plant grown from the corn seed of claim 10.

12. The method of claim 9 further comprising crossing said inbred maize plant with a second maize plant.

13. The method of claim 9 further comprising backcrossing said inbred maize plant with another maize plant.

14. A seed of maize inbred line designated 11Aspo, a representative sample of seed having been deposited under ATCC Accession No. PTA-6978.

15. A maize plant, or a part thereof, produced by growing the seed of claim 14.

16. Pollen of the plant of claim 15.

17. An ovule of the plant of claim 15.

18. A tissue culture of regenerable cells from the maize plant of claim 15.

19. A tissue culture according to claim 18, wherein cells of the tissue culture or protoplasts produced from the tissue culture are from a tissue selected from the group consisting of leaves, pollen, embryos, roots, root tips, anthers, silks, flowers, kernels, ears, cobs, husks, and stalks.

20. A maize plant regenerated from the tissue culture of claim 18, wherein the regenerated plant has all the morphological and physiological characteristics of inbred line 11Aspo.

21. A seed of maize inbred line designated 97RHspo, a representative sample of seed having been deposited under ATCC Accession No. PTA-6982.

22. A maize plant, or a part thereof, produced by growing the seed of claim 21.

23. Pollen of the plant of claim 22.

24. An ovule of the plant of claim 22.

25. A tissue culture of regenerable cells from the maize plant of claim 22.

26. A tissue culture according to claim 25, wherein cells of the tissue culture or protoplasts produced from the tissue culture are from a tissue selected from the group consisting of leaves, pollen, embryos, roots, root tips, anthers, silks, flowers, kernels, ears, cobs, husks, and stalks.

27. A maize plant regenerated from the tissue culture of claim 25, wherein the regenerated plant has all the morphological and physiological characteristics of inbred line 97RHspo.

* * * * *